United States Patent [19]

Yasuhara et al.

[11] 4,067,915

[45] Jan. 10, 1978

[54] METHOD FOR PRODUCING CYCLOHEXANE DERIVATIVES DIRECTLY FROM AROMATIC HYDROCARBONS

[75] Inventors: Yutaka Yasuhara; Masaki Nishino; Seikichi Matsuhisa, all of Nagoya, Japan

[73] Assignee: Toray Industries, Inc., Tokyo, Japan

[21] Appl. No.: 581,788

[22] Filed: May 29, 1975

[30] Foreign Application Priority Data

June 5, 1974 Japan .................................. 49-62844
Nov. 7, 1974 Japan .................................. 49-127523

[51] Int. Cl.² ............................................ C07C 23/10
[52] U.S. Cl. .......................... 260/648 R; 260/631 H; 560/231
[58] Field of Search ............................. 260/648 R, 667

[56] References Cited

U.S. PATENT DOCUMENTS

| | | | |
|---|---|---|---|
| 1,960,977 | 5/1934 | Pier et al. | 260/667 |
| 2,238,594 | 4/1941 | Malishev | 260/667 |
| 2,573,695 | 11/1951 | Dolnick et al. | 260/648 R |

*Primary Examiner*—D. Horwitz
*Attorney, Agent, or Firm*—Miller and Prestia

[57] ABSTRACT

Cyclohexane derivatives such as cyclohexanol, cyclohexyl halides and cyclohexyl carboxylates are produced directly from aromatic hydrocarbons.

The reaction may be carried out, under hydrogenation conditions, by reacting an aromatic hydrocarbon with hydrogen and a reagent selected from the group consisting of water, hydrogen halides and carboxylic acids in the presence of a strong acid and a hydrogenation catalyst.

20 Claims, No Drawings

METHOD FOR PRODUCING CYCLOHEXANE DERIVATIVES DIRECTLY FROM AROMATIC HYDROCARBONS

This invention relates to a method for producing cyclohexane derivatives. More specifically this invention relates to a method for producing a cyclohexane derivative represented by following formula (I) directly from an aromatic hydrocarbon:

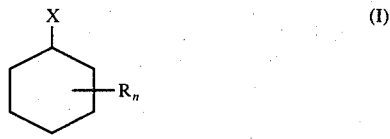

wherein X is halogen, an OH or OAc group, wherein Ac is an acyl group having 1 to 3 carbon atoms, R is a lower alkyl group having 1 to 3 carbon atoms, and $n$ is an integer from 0 to 2.

The cyclohexane derivatives are very important raw materials in synthetic chemical industries. Cyclohexanol and its ester derivatives are used as raw materials for making synthetic polymers or solvents.

Heretofore, various methods for producing cyclohexanols have been proposed. Cyclohexanol, for example, can be produced by oxidation of cyclohexane with molecular oxygen in the presence of a boric acid catalyst or a transition metal catalyst such as cobalt naphthenate. Cyclohexanol can also be obtained by hydrogenation of phenol which can be produced by oxidation of cumene, prepared from benzene. All of these methods used for commercial production of cyclohexanol have hydrogenation and oxidation steps. So far as the hydrogenation process step is concerned, the conversion of the starting materials and the selectivity of the products are substantially quantitative. But the oxidation process step for introducing a hydroxyl group onto the benzene nucleus or into the cyclohexane ring is only barely satisfactory, because the process step often includes complex operations or the percentage conversion in the process step should be kept comparatively low in order to obtain products with a high selectivity.

The halogenated derivatives of cyclohexane have usually been produced by halogenation of cyclohexane or by reaction of cyclohexanol with hydrogen halides. In the former method expensive and toxic molecular halogen should be used and a large amount of hydrogen halide is obtained as a byproduct. The latter method inevitably has the same problem as mentioned above in respect of cyclohexanols.

The cyclohexane derivatives of formula (I) can be produced from cyclohexene in comparatively good yield. Therefore if cyclohexene can be obtained from benzene by selective hydrogenation, this route from benzene to the cyclohexane derivatives is expected to be a good method for producing the cyclohexane derivatives. Thus, some methods of selective hydrogenation of benzene to cyclohexene have been proposed in U.S. Pat. Nos. 3,391,206 and 3,793,383 etc., and in German Application No. 2,221,137.

In these known methods, however, the conversion of benzene should usually be kept at an extremely low level to obtain a high selectivity of cyclohexene, because cyclohexene is hydrogenated more easily than benzene. In some cases a catalyst of complex composition must be used in the selective hydrogenation. Therefore the industrial application of the method is very difficult.

Thus, the object of the present invention is to provide a method for producing cyclohexane derivatives represented by formula (I) directly from benzene and its derivatives, in one step.

We now have found that the cyclohexane derivatives having the general formula (I) can be obtained by allowing the aromatic hydrocarbon to react with a compound HX, wherein X is the same as mentioned above, under hydrogenation conditions in the presence of a strong acid and a hydrogenation catalyst.

The type of aromatic hydrocarbon used as a starting material is not essentially restricted, but from the practical point of view benzene derivatives having a few alkyl substituents having a carbon number of 1 to 3 are preferable. For example benzene, toluene, ethylbenzene, cumene and xylenes are preferably used. Benzene is most preferable. The quality of the aromatic hydrocarbon is also not specifically restricted, so far as it does not contain impurities which cause the activity of the hydrogenation catalyst to deteriorate. An aromatic hydrocarbon which may be fed to a conventional hydrogenation process is preferably used in the present invention.

The amount of the aromatic hydrocarbon may be 0.1 to 40 mol%, preferably 2.0 to 40 mol%, on the basis of the total amount of the aromatic hydrocarbon and the reagent HX.

The reagent HX may be water, a hydrogen halide such as hydrogen chloride, bromide, and iodide, or a carboxylic acid. The carboxylic acids having 1 to 3 carbon atoms such as formic, acetic and propionic acids are preferably used. Acetic acid is most preferable among the carboxylic acids.

The strong acid used in the present invention may be a protonic acid having an acidic dissociation constant pKa of less than 4.0, preferably 3.0, or a Lewis acid having an acid-acting property comparable thereto and having stability under reaction conditions in the present invention. The strong acid may be sulfuric acid, hydrogen chloride, hydrogen bromide, hydrogen iodide, phosphoric acid, an acidic sulfate such as potassium bisulfate, ammonium bisulfate, trifluoroacetic acid, trifluoromethanesulfonic acid, an alkanesulfonic acid, cation exchange resin, boron trifluoride, heteropolyacid such as phosphotungstic acid, silicotungstic acid, phosphomolybdic acid, or silicomolybdic acid, an aromatic sulfonic acid such as benzenesulfonic acid, toluenesulfonic acid, or a solid acid such as alumina, silica alumina, crystalline aluminosilicate, titania or a mixture thereof, etc.

The presence of the strong acid in the reaction mixture is essential to the invention. The amount of the strong acid may preferably be more than 0.01 mol% on the basis of the reagent HX which exists in the reaction mixture. A still more preferable amount is more than 2 mol%.

When the reagent HX is a hydrogen halide, it also can play a role as a strong acid, and it is not necessary to add a strong acid other than that. When the reagent HX is $H_2O$ or a carboxylic acid, at least one strong acid should be added to the reaction mixture.

The cyclohexylester of the strong acid tends to be produced in a relatively large amount, when a strong acid having protonic oxygen is used in a high concentration. For practical purposes, such an ester is hydrolyzed to form a cyclohexane derivative of formula (I), and is thereafter recovered from the reaction mixture. In the present invention the conversion of the aromatic hydrocarbon may preferably be less than 80%. At a conversion of more than 80%, the selectivity of the cyclohexane derivative (I) becomes comparatively low.

The hydrogenation catalyst used in the present invention may usually contain Group VIII metals or its compounds. The Group VIII metals may preferably be noble metals selected from the group consisting of ruthenium, rhodium, palladium, iridium and platinum. Ruthenium, rhodium, and palladium are more preferable. The catalyst may contain at least one noble metal and the combined use of two or more metals may be effective, and may fall within the range of this invention. The noble metal catalyst may be used in an optional form. The usual hydrogenation catalysts for aromatic hydrocarbons may be used in the present invention.

The noble metal catalyst may be in a form of sponge, fine powder, colloid, and supported form. For example, active carbon, alumina, silica, silicaalumina, boria, tungsten trioxide, molybdenum trioxide, zeolites, asbestos, other known solid acids and cationexchange resins may be used as carrier. Some acidic carriers may play a role as the strong acid. An alloy of the noble metal with other metals such as copper, silver, and gold may also be used.

The quality of hydrogen gas used in the present invention is not specifically restricted, except that the hydrogen may not contain impurities deteriorating the activity of the hydrogenation catalyst. Hydrogen may contain an inert gas such as nitrogen, helium, argon, carbon dioxide or methane.

A pressure of hydrogen does not essentially influence the reaction of the present invention. Preferable partial pressure of hydrogen is 0.01 to 300 Kg/cm$^2$, preferably 0.5 to 150 Kg/cm$^2$. In view of the reaction rate and the pressure restriction of the reaction apparatus, the reaction may preferably carried out under a pressure of 0.01 – 500 Kg/cm$^2$, more preferaby 0.5 – 150 Kg/cm$^2$. The reaction temperature is 0° – 300° C, preferably 20° – 200° C.

In the embodiments of the present invention, the reaction may be carried out in an inert solvent such as methanol, dioxane, cyclohexane or n-octane, etc.

The reaction products of the present invention are mainly cyclohexane derivatives of formula (I) and cyclohexane or its alkyl derivatives. In some cases, cyclohexene, phenylcyclohexan, cyclohexanone, or their alkyl derivatives are produced. The amounts of other byproducts are negligible under usual reaction conditions. The recovery of the cyclohexane derivatives (I) from the reaction mixture can be easily carried out according to conventional methods. The reaction of the present invention may be carried out either continuously or batchwise.

The mechanisms of the reaction in this invention have not been clearly understood, but the practical superiority of the present invention may be explained as follows in comparison with the selective hydrogenation of benzene to cyclohexene mentioned above. In the latter reaction, it is very difficult to enhance the conversion of benzene without sacrificing the selectivity of cyclohexene, because cyclohexene is more easily hydrogenated than benzene. On the other hand, in the former reaction which may be referred to as a "hydrogenohydration" process, the products of the formula (I) result from the addition of the reagent HX such as water etc. to an intermediate carbonium ion formed by the protonation of the intermediate cycloolefins which are formed in the hydrogenation step. The products are usually less reducible than benzene, therefore, it is possible to enhance the conversion of benzene to obtain final products of the formula (I) without sacrifice of selectivity.

The following examples will serve to further illustrate the present invention.

The terms, conversion, yield, and selectivity, used in the examples are defined as follows.

conversion (%) =

$$\frac{[\text{amount of reacted aromatic hydrocarbon}]}{[\text{amount of aromatic hydrocarbon charged}]} \times 100$$

yield (%) =

$$\frac{[\text{amount of a product (mols)}]}{[\text{amount of aromatic hydrocarbon charged (mols)}]} \times 100$$

selectivity (%) =

$$\frac{[\text{amount of a product (mols)}]}{[\text{amount of reacted aromatic hydrocarbon (mols)}]} \times 100$$

EXAMPLE 1

In a 100 ml. flask were placed 10 ml. of glacial acetic acid, 4 ml. of benzene, 1 ml. of boron trifluoride-diacetic acid complex, and 0.5 g. of 5% ruthenium on carbon catalyst. Stirring was provided by a bar magnet (sheathed with poly-tetrafluoroethylene) placed inside the flask. The bar magnet was set in motion by an external magnetic stirrer. After the flask was flushed with hydrogen, the contents of the flask were warmed to 70° C for 10 hours at an atmospheric pressure of hydrogen. Then, the flask was chilled in an ice-water bath, and to the flask, 60 ml. of ether was added. The ether layer separated, was washed with 10% sodium carbonate and with saturated sodium chloride, and was subjected to analysis by means of a gas-liquid chromatograph. This analysis showed that 1.2% of the benzene reacted with hydrogen and acetic acid to produce cyclohexyl acetate with a selectivity of 1% along with cyclohexane.

EXAMPLE 2 – 4

Hydrogenation catalysts were examined for activity and selectivity in convertion of benzene to cyclohexyl acetate. In each experiment, an appointed volume of glacial acetic acid, an appointed volume of benzene, 1 ml. of boron trifluoride-diacetic acid complex and an appointed amount of hydrogenation catalyst were treated at atmospheric pressure of hydrogen in a manner similar to that set forth im Example 1. The following table shows the reaction conditions and the results obtained.

Table I

| Example No. | Acetic acid (ml) | Reaction conditions | | | | Products | |
|---|---|---|---|---|---|---|---|
| | | Benzene (ml) | Catalyst (mg) | Temp. (° C) | Time (hr) | Yield of Cyclohexane(%) | Selectivity of Cyclohexyl acetate(%) |
| 2 | 13 | 5 | 5%Ru/C200 | 75 | 12 | 0.8 | 5 |
| 3 | 10 | 4 | 9%Pd/C500 | 70 | 6 | 4 | 1 |

Table I-continued

| Example No. | Acetic acid (ml) | Reaction conditions | | | | Products | |
|---|---|---|---|---|---|---|---|
| | | Benzene (ml) | Catalyst (mg) | Temp. (° C) | Time (hr) | Yield of Cyclo-hexane(%) | Selectivity of Cyclohexyl acetate(%) |
| 4 | 10 | 4 | PtO$_2$200 | 70 | 6 | 12 | 0.6 |

EXAMPLE 5

In a manner similar to that set forth in Example 1, 5 ml. of benzene, 13 ml. of 50% sulfuric acid, and 0.5 g of 5% ruthenium on carbon, were treated under atmospheric pressure of hydrogen, at 70° C for 12 hours. The analysis of the reaction mixture by means of a gas-liquid chromatograph, showed that 1.1% of the benzene was converted into cyclohexanol with a selectivity of 1.8%.

EXAMPLE 6

In a high pressure glass bomb with a bar magnet (sheathed with polytetrafluoroethylene) set in motion by an external magnetic stirrer, were placed 10 ml. of glacial acetic acid, 4 g of benzene, 1 ml. of boron trifluoride-diacetic acid complex, and 0.2 g of 5% ruthenium on carbon catalyst. The bomb and the contents thereof were heated at 75° C, pressured with 5 Kg/cm$^2$G of hydrogen, for 1 hour. Then, the bomb was chilled in an ice-water bath, and the reaction mixture was treated in a manner similar to that set forth in Example 1 and subjected to analysis by means of gas-liquid chromatography. This analysis showed that cyclohexyl acetate was produced with a selectivity of 3.4% along with cyclohexane from 5.2% of benzene initially charged.

EXAMPLE 7 – 24

In each experiment, 1 ml. of acetic acid, 1 g. of benzene, 0.5 ml. of boron trifluoride-diacetic acid complex, and 50 mg. of a hydrogenation catalyst were treated at 75° C and 5 Kg/cm$^2$G of hydrogen in a manner similar to that set forth in Example 6. The following table shows the results obtained.

Table II

| Example No. | Catalyst | Time (hr) | Yield of Cyclo-hexane(%) | Selectivity of Cyclohexyl acetate(%) |
|---|---|---|---|---|
| 7 | 1%Pd/C | 20 | 3.1 | 0.6 |
| 8 | 2%Pd/Sio$_2$ | 20 | 8.4 | 0.7 |
| 9 | 2%Pd/Al$_2$O$_3$ | 20 | 2.8 | 3.2 |
| 10 | 2%Pd/WO$_3$ | 20 | 1.0 | 2.0 |
| 11 | 2%Rh/SiO$_2$ | 3.3 | 17.3 | 0.5 |
| 12 | 2%Rh/Zeolite | 4.1 | 9.4 | 0.5 |
| 13 | 2%Rh/WO$_3$ | 3.6 | 18.0 | 0.5 |
| 14 | 2%Rh/Al$_2$O$_3$ | 2.3 | 20.3 | 0.7 |
| 15 | 2%Rh/C | 6.5 | 17.0 | 0.9 |
| 16 | 2%Ru/SiO$_2$ | 20 | 0.9 | 16.7 |
| 17 | 2%Ru/Al$_2$O$_3$ | 20 | 0.3 | 18.5 |
| 18 | 2%Ru/Zeolite | 20 | 0.2 | 7.2 |
| 19 | 2%Ru/WO$_3$ | 18.3 | 11.5 | 4.7 |
| 20 | 2%Pt/C | 6 | 13.1 | 0.6 |
| 21 | 2%Pt/SiO$_2$ | 0.5 | 21.7 | 0.1 |
| 22 | 2%Pt/WO$_3$ | 5 | 17.6 | 0.5 |
| 23 | 2%Ir/C | 3.5 | 9.8 | 0.2 |
| 24 | 2%Ir/Al$_2$O$_3$ | 1.8 | 17.6 | 0.1 |

EXAMPLE 25

In a manner similar to that set forth in Example 6, 4 g. of benzene, 8ml. of 55% sulfuric acid, and 0.2 g. of 5% ruthenium on carbon were treated. After reaction at 70° C and at an atmospheric pressure of hydrogen, for 45 minutes, the reaction mixture was analyzed by means of a gas-liquid chromatograph. The data showed that 6% of the benzene was converted into cyclohexanol with a selectivity of 1.5%.

EXAMPLE 26

A palladium-containing cation exchange resin was prepared from 3.5 g of tetraammine palladium (II) dichloride; Pd(NH$_3$)$_4$Cl$_2$, 30 g of Amberlyst 15 (a cation exchange resin supplied from Rohm & Haas Co.) in the sodium form. They were mixed in 300 ml. of distilled water, for 90 min., and filtered. The solid was washed with distilled water, then with ethanol, and dried at 100° C under reduced pressure. The resin was treated with 300 ml. water and 80 ml. of an 80% aqueous solution of hydrazine, at 80° C for 40 min., and filtered. The resin was placed on a column and eluted with 5% aqueous hydrochloric acid, and washed with about 2000 ml. water (at that point it was chloride free), then with alcohol and finally with ether. It was dried at 100° C for 2 hours under reduced pressure. The product was a catalyst comprising a ion exchange resin of sulfonic acid type which includes zero valent palladium in its resin matrix.

The catalyst was used for the hydrogenohydration of benzene. In a manner similar to that set forth in Example 6, 3 ml. of glacial acetic acid, 2 g. of benzene, and 0.2 g of the said catalyst were heated at 110° C for 20 hours under hydrogen at 5 Kg/cm$^2$G. The analysis of the reaction mixture by means of a gas-liquid chromatograph showed that 4.6% of the benzene was converted into cyclohexyl acetate with a selectivity of 0.3%.

EXAMPLE 27 – 31

In a manner similar to that set forth in Example 26, the preparation of catalysts and the hydrogenohydration of benzene were carried out. In each case, 3 ml. of glacial acetic acid, 2 g. of benzene, and 0.2 g. of a catalyst were treated under 5 Kg/cm$^2$G of hydrogen at an appointed temperature for an appointed time. The following table shows the results obtained.

Table III

| Example No. | Catalyst | Temp. (° C) | Time (hr) | Yileld of Cyclohexane(%) | Selectivity of Cyclohexyl acetate(%) |
|---|---|---|---|---|---|
| 27 | Pd/Amberlyst 15 | 95 | 15 | 4.7 | 0.1 |
| 28 | Pd/Amberlite200 | 95 | 15 | 1.1 | 0.2 |
| 29 | Rh/Amberlyst15 | 75 | 4 | 7.2 | 0.3 |
| 30 | Rh/Amberlite200 | 75 | 4 | 17.2 | 0.1 |
| 31 | Ru/Amberlite200 | 75 | 30 | 5.8 | 1.5 |

In Table III, the following notes are applicable: in Example 27, the same catalyst as that of Example 8 was used. In Example 28, the catalyst was prepared by using 0.7g. of Pd(NH$_3$)$_4$Cl$_2$ and 15g. of Amberlite 200 (a cation-exchange resin from Rohm and Haas Co.). In examples 29 and 30, each catalyst was prepared by using 0.5g. of rhodium trichloried trihydrate and 5g. of Amberlyst 15 or Amberlite 200. In Example 31, the catalyst was prepared by using 0.5g. of ruthenium trichloride monohydrate and 5g. of Amberlite 200. In Examples 29 and 30, the ruthenium and rhodium compounds were reduced to a zero-valent state by formalin in an aqueous solution of sodium hydroxide instead of hydrazine.

were treated at 75° C and 5 Kg/cm²G of hydrogen. The following table shows the results obtained.

Table VI

| Example No. | Aromatic hydrocarbon | Carboxylic acid | Time (hr) | Acid-acting catalyst | Conversion of aromatic hydrocarbon (%) | Selectivity of ester (%) |
|---|---|---|---|---|---|---|
| 43 | Toluene | Acetic acid | 5 | $BF_3 \cdot 2CH_3COOH$ 1ml | 6.3 | Methycyclohexyl acetates 1.3 |
| 44 | Ethylbenzene | Acetic acid | 24 | $BF_3 \cdot 2CH_3COOH$ 1ml | 17.2 | Ethycyclohexyl acetates 0.7 |
| 45 | Benzene | Propionic acid | 8 | Phosphotungstic acid 0.1g | 7.4 | Cyclohexyl propionate 0.5 |

EXAMPLES 32 – 37

In a manner similar to that set forth in Example 6, 2g. of benzene, 3g of glacial acetic acid, 0.1g. of a hydrogenation catalyst, and 0.1g of a heteropolyacid catalyst were treated at 95° C and 5 kg/cm²G of hydrogen. The following table shows the results obtained.

Table IV

| Ex. No. | Catalyst | Heteropoly acid | Time (hr) | Yield of Cyclohexane(%) | Selectivity of Cyclohexyl actate(%) |
|---|---|---|---|---|---|
| 32 | 2%Ru/SiO₂ | PW-acid | 31 | 2.7 | 27.3 |
| 33 | 2%Ru/WO₃ | PW-acid | 31 | 7.5 | 10.7 |
| 34 | 2%Pd/SiO₂ | PW-acid | 15 | 15.1 | 1.4 |
| 35 | 2%Pd/WO₃ | PW-acid | 15 | 11.1 | 3.3 |
| 36 | 2%Ru/WO₃ | SW-acid | 24 | 3.5 | 17.9 |
| 37 | 2%Pd/WO₃ | SW-acid | 13 | 5.3 | 8.9 |

*PW-acid and SW-acid represent phosphotungstic acid and silico-tungstic acid, respectively.

EXAMPLES 38 – 42

In a manner similar to that set forth in Example 6, formic acid and benezene were treated in the presence of a hydrogenation catalyst and an acid-acting catalyst. After a reaction time of 24 hours the analysis of the reaction mixture by means of a gas-liquid chromatograph showed that cyclohexyl formate was the sole product. The following table shows the reaction conditions and the results obtained.

Table V

| Example No. | Reactants & Catalysts | | | H₂ (kg/cm²G) | Temp. (° C) | Yield of Cyclohexyl formate(%) |
|---|---|---|---|---|---|---|
| | Benzene (g) | HCOOH (ml) | Catalyst (mg) | | | |
| 38 | 1.0 | 1.5 | 1%Pd/MoO₃ PW-acid* 100 | 5 | 95 | 0.007 |
| 39 | 1.0 | 0.75 | 5%Ru/C 50 BF₃·2AcOH100 | 5 | 75 | 0.002 |
| 40 | 1.6 | 5 | 2%Rh/C 200 PW-acid 100 | 10 | 95 | 0.002 |
| 41 | 1.6 | 5 | 2%Pt/WO₃ 200 PW-acid 100 | 10 | 95 | 0.001 |
| 42 | 1.6 | 5 | 2%Ir/WO₃ 200 PW-acid 100 | 10 | 95 | 0.001 |

PW-acid represents phosphotungstic acid.
*Palladium (1% by weight) is supported on a mixture of molybdenum trioxide and phosphotungstic acid (4:1 by weight).

EXAMPLES 43 – 45

In a manner similar to that set forth in Example 6, 2g. of an aromtic hydrocarbon, 4 ml. of a carboxylic acid, and 0.1g. of 5% ruthenium on activated carbon catalyst

EXAMPLES 46 – 49

In a manner similar to that set forth in Example 6, 1g. of benzene, 2 ml. of 50% aqueous solution of sulfuric acid, and 20 mg. of a hydrogenation catalyst were treated at 70° C and 50 Kg/cm²G of hydrogen. The following table shows the results obtained.

Table VII

| Example No. | Hydrogenation catalyst | Time (hr) | Yield of cyclohexane (%) | Selectivity of cyclohexanol (%) |
|---|---|---|---|---|
| 46 | 2%Ru/WO₃ | 25 | 4.3 | 0.1 |
| 47 | 2%Ru/Al₂O₃ | 24 | 1.1 | 0.7 |
| 48 | 2%Ru/SiO₂ | 18 | 1.0 | 0.6 |
| 49 | 2%Ru/Zeolite | 18 | 0.8 | 0.2 |

EXAMPLES 50 – 54

In a manner similar to that set forth in Example 6, 1g. of benzene, 2 ml. of 50% sulfuric acid, 20 mg. of a hydrogenation catalyst and an appointed amount of an organic solvent were treated at 70° C and 50 Kg/cm²G of hydrogen. The following table shows the results obtained.

Table VIII

| Ex. No. | Hydrogenation catalyst | organic solvent (ml) | Time (hr) | Yield of cyclohexane (%) | Selectivity of cyclohexanol (%) |
|---|---|---|---|---|---|
| 50 | 2%Ru/c | CH₃COOH 0.1 | 24 | 7.3 | 0.1* |
| 51 | 2%Ru/Al₂O₃ | CH₃COOH 0.1 | 24 | 1.6 | 0.2 |
| 52 | 2%Ru/Al₂O₃ | Dioxane 0.1 | 24 | 1.1 | 0.4 |
| 53 | 2%Ru/Al₂O₃ | Dioxane 0.4 | 24 | 0.8 | 0.5 |
| 54 | 2%Ru/SiO₂ | Methanol 0.1 | 17 | 1.6 | 0.6 |

*Selectivity of cyclohexyl acetate

EXAMPLES 55 – 56

In a manner similar to that set forth in Example 6, 2 ml. of benzene, 5 ml. of water, 0.2 g. of 2% rhodium on WO₃ catalyst, and an appointed amount of phosphotungstic acid were treated at 95° C and 10 Kg/cm²G of hydrogen for 24 hours. The following table shows the results obtained.

hydrogen. The following table shows the results obtained.

Table XII

| Example No. | Hydrogenation catalyst | Reaction temperature (° C) | Reaction time (hr) | Yield of cyclohexane (%) | Selectivity of cyclohexanol (%) |
|---|---|---|---|---|---|
| 80 | 2%Ru/SiO₂ | 60 | 24 | 2.4 | 0.75 |
| 81 | 2%Ru/SiO₂ | 100 | 24 | 1.0 | 0.68 |
| 82 | 2%Ru/SiO₂ | 100 | 24 | 15.4 | 0.19 |
| 83 | 2%Rh/SiO₂ | 60 | 16 | 45.3 | 0.03 |
| 84 | 2%Rh/SiO₂ | 80 | 7 | 29.2 | 0.05 |
| 85 | 2%Rh/SiO₂ | 100 | 7.5 | 7.1 | 0.17 |

Table IX

| Ex. No. | Amount of phosphotungstic acid (g) | Yield of cyclohexane (%) | Selectivity of cyclohexanol (%) | Selectivity of cyclohexene (%) |
|---|---|---|---|---|
| 55 | 1.0 | 1.6 | 0.07 | 0 |
| 56 | 2.0 | 9.5 | 0.21 | 10.3 |

EXAMPLES 57 – 67

In a manner similar to that set forth in Example 6, 1g. of benzene, 2 ml. of 50% sulfuric acid, 0.4 ml. of methanol, and 20 mg. of a hydrogenation catalyst were treated at 70° C. The following table shows the results obtained.

Table X

| Ex. No. | Hydrogenation catalyst | Hydrogen pressure (Kg/cm²G) | Time (hr) | Yield of cyclohexane (%) | Selectivity of cyclohexanol (%) |
|---|---|---|---|---|---|
| 57 | 2%Rh/Al₂O₃ | 5 | 6 | 32 | 0.08 |
| 58 | 2%Rh/WO₃ | 5 | 7 | 12 | 0.17 |
| 59 | 2%Rh/Zeolite | 2 | 24 | 6.9 | 0.09 |
| 60 | 2%Rh/Sio₂ | 2 | 24 | 2.5 | 1.2 |
| 61 | 2%Rh/SiO₂ | 3 | 24 | 56 | 0.98 |
| 62 | 2%Rh/SiO₂ | 10 | 6.25 | 16 | 0.19 |
| 63 | 2%Rh/SiO₂ | 20 | 2 | 23.2 | 0.03 |
| 64 | 2%Ru/SiO₂ | 5 | 24 | 0.63 | 1.75 |
| 65 | 2%Ru/SiO₂ | 10 | 6 | 1.76 | 0.46 |
| 66 | 2%Ru/SiO₂ | 20 | 24 | 8.1 | 0.26 |
| 67 | 2%Ru/SiO₂ | 40 | 24 | 20.6 | 0.14 |

EXAMPLES 68 – 79

In a manner similar to that set forth in Example 6, 1g. of benzene, 2 ml. of 50% sulfuric acid, 20 mg. of a hydrogenation catalyst, and an appointed amount of a sulfate were treated at 70° C and 5 Kg/cm²G of hydrogen. The following table shows the results obtained.

Table XI

| Example No. | Catalyst | Sulfate (g) | Time (hr) | Yield of cyclohexane (%) | Selectivity of cyclohexanol (%) |
|---|---|---|---|---|---|
| 68 | 2%Ru/Al₂O₃ | NaHSO₄ · H₂O (1.85) | 24 | 0.92 | 0.44 |
| 69 | 2%Ru/SiO₂ | NaHSO₄ · H₂O (0.4) | 24 | 0.56 | 1.07 |
| 70 | 2%Rh/SiO₂ | NaHSO₄ · H₂O (0.04) | 7 | 16.7 | 0.19 |
| 71 | 2%Rh/SiO₂ | Ti(SO₄)₂ · 4H₂O (1) | 24 | 0.6 | 1.5 |
| 72 | 2%Rh/Sio₂ | Cr(SO₄)₃ · 9H₂O (1) | 6 | 4.8 | 0.27* |
| 73 | 2%Rh/SiO₂ | In₂(SO₄)₃ · 9H₂O (1) | 24 | 1.3 | 0.38 |
| 74 | 2%Rh/SiO₂ | Th(SO₄)₂ · 9H₂O (1) | 6.5 | 8.8 | 0.23* |
| 75 | 2%Rh/SiO₂ | Ag₂SO₄ (1) | 7.25 | 1.5 | 1.87 |
| 76 | 2%Rh/SiO₂ | BeSO₄ · 4H₂O (1) | 23 | 0.4 | 0.75 |
| 77 | 2%Rh/SiO₂ | CdSO₄ (1) | 7 | 7.5 | 0.59* |
| 78 | 2%Rh/SiO₂ | La₂(SO₄)₃ · 9H₂O (1) | 24 | 4.1 | 0.39 |
| 79 | 2%Rh/SiO₂ | UO₂SO₄ · 3H₂O (1) | 7 | 5.6 | 0.36 |

*Some amounts of cyclohexanone were also detected.

EXAMPLES 80 – 85

In a manner similar to that set forth in Example 6, 1g. of benzene, 2 ml. of 50% sulfuric acid, and 0.1 g. of a hydrogenation catalyst were treated at 5 Kg/cm²G of hydrogen. The following table shows the results obtained.

EXAMPLES 86 – 92

In a manner similar to that set forth in Example 6, 2 g. of benzene, 3 ml. of glacial acetic acid, and 0.2 g. of a catalyst were treated at 95° C and 5 Kg/cm²G of hydrogen. The following table shows the results obtained.

Table XIII

| Ex. No. | Catalyst | Time (hr) | Yield of cyclohexane (%) | Selectivity of cyclohexyl acetate (%) |
|---|---|---|---|---|
| 86 | 1%Pd/Neobead MSC | 15 | 17.1 | 0.02 |
| 87 | 1%Pd/Neobead P | 15 | 6.5 | 0.05 |
| 88 | 1%Pd/Silbead W | 15 | 33.4 | 0.03 |
| 89 | 1%Ru/Zeolite LaY | 30 | 2.7 | 0.17 |
| 90 | 1%Rh/Zeolite LaY | 7 | 13.1 | 0.04 |
| 91 | 1%Pd/Zeolite HY | 23 | 5.3 | 0.02 |
| 92 | 2%Pd/TiO₂—Al₂O₃ | 16 | 26.3 | 0.02 |

In Table XIII, the following notes are applicable: In Examples 86 to 88, Neobead MSC is composed of Al₂O₃, Neobead P of 88% Al₂O₃, 9% SiO₂, and 3% Na₂O by weight and Silbead W of 12% Al₂O₃ and 88% SiO₂. These were obtained from Mizusawa Industrial Chemicals Ltd.

In Examples 89 to 91, Zeolite Y was obtained from Union Carbide Co.

In Example 92, a binary metal oxide, TiO₂-Al₂O₃, was prepared by a conventional co-precipitation method from a mixture of titanium chloride and aluminum nitrate as 1:9 molar ratio.

EXAMPLE 93

A mixture of 5 g. of benzene, 50 ml. of 20% hydrochloric acid, and 300 mg. of 2% rhodium on silica was put into a 40 ml. flask of an atmospheric hydrogenation apparatus, and heated under atmospheric pressure of hydrogen at 60° C for 23 hours. After separation from the reaction mixture, the organic layer was dried with 0.5 g of anhydrous potassium carbonate, and submitted to gas-liquid chromatography. The data indicated that 0.13% of the benzene was hydrogenated, producing cyclohexylchloride and cyclohexane with 47.7% and 52.3% selectivity, respectively.

EXAMPLE 94

A charge of 5 ml. of benzene, 15 ml. of 30% hydrobromic acid, and 300 mg. of 2% rhodium on silica was heated under atmospheric pressure of hydrogen at 60° C for 23 hours as described in Example 93. The gas-liquid chromatogram of the products indicated that cyclohexylbromide with 31.6% selectivity was produced from 0.12% of the benzene of the initial charge.

EXAMPLE 95

A mixture of 5 ml. of benzene, 15 ml. of 20% hydrochloric acid, 3 g. of sodium chloride, and 300 mg. of 2% rhodium on silica was heated under the identical conditions as described in Example 93. The gas-liquid chromatogram of the products indicated that 0.13% of the benzene was converted into cyclohexylchloride with 63.8% selectivity.

EXAMPLE 96

A charge of 2 ml. of benzene, 5 ml. of 35% hydrochloric acid, and 200 mg. of 5% rhodium on silica was placed in a 20 ml. glass bomb and heated under 20 Kg/cm²G pressure of hydrogen at 75° C, for 20 hours. The organic layer was submitted to gas-liquid chromatography and the data indicated that 13.4% of the benzene was converted into cyclohexylchoride and cyclohexane with 34% and 66% selectivity, respectively.

EXAMPLE 97 – 99

These experiments were carried out in the same manner as described in Example 96 and the data are summarized in Table XIV.

Table XIV

| Example No. | Catalyst | Conversion of benzene (%) | Selectivity of cyclohexylchloride (%) |
|---|---|---|---|
| 97 | 2%Pd/SiO$_2$ | 1.3 | 18 |
| 98 | 2%Pt/SiO$_2$ | 3.4 | 17* |
| 99 | 2%Ir/SiO$_2$ | 0.47 | 21 |

Reaction conditions:
Benzene 2ml, 35%HCl 5ml, Catalyst 200mg. H$_2$ 3Kg/cm²G, 75° C, 20hr.
*Some cyclohexene was also detected.

EXAMPLES 100 – 104

These runs were performed in the same manner as described in Example 96 and the data are summarized in Table XV.

Table XV

| Example No. | Catalyst | Aromatic hydrocarbon | Yield of alkyl-cyclohexane (%) | Yield of chlorinated alkylcyclohexanes (%) |
|---|---|---|---|---|
| 100* | 2%Rh/SiO$_2$ | Toluene | Methylcyclohexane 7.7 | Chloromethylcyclohexanes 0.9 |
| 101 | 2%Rh/SiO$_2$ | Toluene | 0.19 | 0.33 |
| 102 | 2%Rh/SiO$_2$ | p-Xylene | 1,4-Dimethylcyclohexane 0.08 | Chlorodimethylcyclohexanes 0.02 |
| 103 | 10%Rh/SiO$_2$ | Ethylbenzene | Ethylcyclohexane 0.32 | Chlorethylcyclohexanes 0.38 |
| 104 | 10%Rh/SiO$_2$ | Cumene | Isopropylcyclohexane 0.26 | Chloroisopropylcyclohexanes 0.17 |

Reaction conditions:
Aromatic hydrocarbon 2ml. 35%HCl 5 ml., Catalyst 200mg., H$_2$ 3Kg/cm²G, 75° C, 20hr.
*Toluene 1g., 20% HCl 2ml., Catalyst 50mg., H$_2$ 5Kg/cm²G. 70° C, 24 hr.

EXAMPLES 105 – 108

These runs were practiced in the same manner as described in Example 96 and the data were summarized in Table XVI.

Table XVI

| Example No. | Hydrogen halide | H$_2$ (Kg/cm²G) | Yield of cyclohexane (%) | Yield of Halo-cyclohexane (%) |
|---|---|---|---|---|
| 105 | 47%HBr | 3.0 | 0.031 | 0.044 * |
| 106 | 38%HBr | 3.0 | 0.080 | 0.008 |
| 107 | 28%HBr | 3.0 | 0.33 | 0.02 |
| 108 | 36%HI | 5.0 | 0.067 | 0.006 |

Reaction conditions:
Benzene 2ml., Aqueous hydrogen halide 5ml., Catalyst 10%Rh/SiO$_2$ 200mg., 75° C. 20hr.
* Some cyclohexene was also detected.

EXAMPLE 109

A mixture of 1g. of benzene, 2 ml. of 35% hydrochloric acid, and 50 mg. of 2% rhodium on active carbon was heated under 5.0 Kg/cm²G pressure of hydrogen at 70° C for 24 hours. The gas-liquid chromatogram of the products indicated that 3.5% of the benzene was converted into cyclohexylchloride and cyclohexane with 2% and 98% selectivity, respectively.

EXAMPLES 110 – 111

These examples were performed in the same manner as described in Example 96 and the data are tabulated in Table XVII.

Table XVII

| Example No. | Catalyst | Temp. (° C) | Time (hr) | Yield of cyclohexane (%) | Yield of chlorocyclohexane (%) |
|---|---|---|---|---|---|
| 110 | 2%Rh/SiO$_2$ 1.0g. | 80 | 22 | 2.0 | 3.5 |
| 111 | 10%RhCl$_3$ aq. | 95 | 40 | 4.9 | 1.1 |

Table XVII-continued

| Example No. | Catalyst | Temp. (° C) | Time (hr) | Yield of cyclohexane (%) | Yield of chloro-cyclohexane (%) |
| --- | --- | --- | --- | --- | --- |
| | soln. 0.1 ml. | | | | |

Reaction conditions: Benzene 1 ml., 35%HCl 2 ml., H$_2$ 3 · 0Kg/cm$^2$G.
* In this case, a mirror of Rh was formed on the wall of the glass bomb.

EXAMPLES 112 – 117

These runs were carried out in the same manner as described in Example 96 and the data are summarized in Table XVIII.

Table XVIII

| Example No. | Catalyst | Temp. (° C) | Yield of cyclohexane (%) | Yield of chlorocyclo-hexane (%) |
| --- | --- | --- | --- | --- |
| 112 | 0.2%Rh/SiO$_2$ | 75 | 0.01 | 0.01 |
| 113 | 1 %Rh/SiO$_2$ | 75 | 0.05 | 0.08 |
| 114 | 5 %Rh/SiO$_2$ | 75 | 0.55 | 0.28 |
| 115 | 10 %Rh/SiO$_2$ | 75 | 0.76 | 0.39 |
| 116 | 2 %Rh/SiO$_2$ | 60 | 0.09 | 0.11 |
| 117 | 2 %Rh/SiO$_2$ | 100 | 0.01 | 0.02 |

Reaction Conditions: Benzene 2ml., 35% HCl 5ml., H$_2$ 3Kg/cm$^2$G, 20hr.

EXAMPLE 118 – 128

These examples were praticed in the same manner as described in Example 96, and the data are summarized in Table XIX.

Table XIX

| Ex. No. | Concentration of HCl (%) | Temp. (° C) | H$_2$ (Kg/cm$^2$G) | Yield of cyclo-hexane (%) | Yield of chloro-cyclohexane (%) |
| --- | --- | --- | --- | --- | --- |
| 118 | 35 | 75 | 1.6 | 0.01 | 0.04 |
| 119 | 35 | 75 | 3.2 | 0.18 | 0.35 |
| 120 | 35 | 75 | 5.5 | 0.57 | 0.75 |
| 121 | 35 | 75 | 8.5 | 0.77 | 0.93 |
| 122 | 16.4 | 75 | 3.0 | 5.4 | 0.05* |
| 123 | 29.5 | 75 | 3.0 | 0.91 | 0.65* |
| 124 | 35 | 65 | 10 | 1.27 | 0.66 |
| 125 | 35 | 90 | 10 | 1.48 | 2.08 |
| 126 | 35 | 100 | 10 | 1.26 | 2.78 |
| 127 | 35 | 120 | 10 | 0.25 | 0.91 |
| 128 | 35 | 75 | 15 | 3.17 | 2.30 |

Reaction conditions:
Benzene 2ml., Hydrochloric acid 5ml., Catalyst 5%Rh/SiO$_2$ 200mg., 20hr.
*Some cyclohexanol cyclohexene were also detected.

EXAMPLE 129

In a glass vessel (ca. 35 ml.) having a coiled capillary vent together with a small bar magnet coated with polytetrafluoroethylene, were charged 2 ml. of benzene and 200 mg. of 10% rhodium on silica. The vessel was placed in a high pressure Hastelloy B bomb (ca. 100 ml.), and swept with dry hydrogen chloride. The bomb was filled with 10 Kg/cm$^2$G of hydrogen chloride and 40 Kg/cm$^2$G of hydrogen, and heated at 120° C while magnetically stirring for 16 hours. After the gas was released, the vessel was taken out, then the organic layer was submitted to gas-liquid chromatography. The data obtained indicated that the yield of cyclohexane and chlorocyclohexane were 35.4% and 1.7%, respectively.

EXAMPLE 130 – 131

These examples were carried out in the same manner as described in Example 129, and the data were tabulated in Table XX.

Table XX

| Ex. No. | Catalyst (mg) | Benzene (ml) | Yield of chloro-cyclohexane (%) | Yield of chloro-hexane (%) |
| --- | --- | --- | --- | --- |
| 130 | 10%Ru/SiO$_2$ 200 | 2 | 0.77 | 0.53 |
| 131 | 10%Ru/SiO$_2$ 200 | 5 | 0.12 | 0.23 |

Reaction conditions: HCl(gas) 10 Kg/cm$^2$G, H$_2$ 40 Kg/cm$^2$G, 120° C, 17hr.

What we claim is:

1. A process for producing a cyclohexane derivative having the general formula

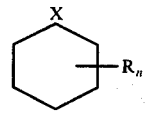

wherein X is selected from the group consisting of chlorine, bromine and iodine R is a lower alkyl group having 1 to 3 carbon atoms, and $n$ is an integer of from 0 to 2, which process comprises reacting an aromatic hydrocarbon having the general formula

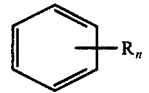

wherein R and $n$ are the same as above, with hydrogen and a compound having the general formula HX, wherein X is the same as above, in the presence of a strong acid and a hydrogenation catalyst that contains at least one noble metal of Group VIII metals at a pressure of 0.01 – 500 Kg/cm$^2$ and at a temperature of 0°–300° C.

2. A process of claim 1, wherein X is chlorine.

3. A process of claim 2, wherein the strong acid is hydrogen chloride.

4. A process of claim 2, wherein the hydrogenation catalyst contains at least one component selected from the group consisting of metals and compounds of metals of Group VIII of the Periodic System.

5. A process of claim 4, wherein the hydrogenation catalyst contains at least one component selected from the group consisting of rhodium, ruthenium, palladium, platinum, iridium, and compounds thereof.

6. A process of claim 2, wherein a carrier is employed in addition to the hydrogenation catalyst.

7. A process of claim 6, wherein the carrier is selected from the group consisting of active carbon, silica, alumina, silica-alumina, boria, tungsten trioxide, molybdenum trioxide, zeolites, asbestos, solid acids and cation-exchange resins.

8. A process of claim 2, wherein the reaction is carried out in an aqueous medium.

9. A process of claim 2, wherein the conversion of the aromatic hydrocarbon is less than 80 percent.

10. A process of claim 1, wherein X is bromine.

11. A process of claim 10, wherein the strong acid is hydrogen bromide.

12. A process of claim 10, wherein the hydrogenation catalyst contains at least one component selected from the group consisting of metals and compounds of metals of Group VIII of the Periodic System.

13. A process of claim 10, wherein the hydrogenation catalyst contains at least one component selected from the group consisting of rhodium, ruthenium, palladium, platinum, iridium, and compounds thereof.

14. A process of claim 10, wherein the reaction is carried out in an aqueous medium.

15. A process of claim 10, wherein the conversion of the aromatic hydrocarbon is less than 80 percent.

16. A process of claim 1, wherein the X is iodine.

17. A process of claim 16, wherein the strong acid is hydrogen iodide.

18. A process of claim 16, wherein the hydrogenation catalyst contains at least one component selected from the group consisting of rhodium, ruthenium, palladium, platinum, and their compounds.

19. A process of claim 16, wherein the reaction is carried out in an aqueous medium.

20. A process of claim 16, wherein the conversion of the aromatic hydrocarbon is less than 80 percent.

* * * * *